(12) United States Patent
Beerwerth et al.

(10) Patent No.: US 11,123,573 B2
(45) Date of Patent: Sep. 21, 2021

(54) SKIN OR HAIR TREATMENT DEVICE AND METHOD FOR MANUFACTURING SAME

(71) Applicant: Braun GmbH, Kronberg (DE)

(72) Inventors: Frank Beerwerth, Kaltenholzhausen (DE); Uwe Bielfeldt, Bad Soden (DE); Dalibor Dadic, Koenigstein (DE); Felix Heinemann, Frankfurt am Main (DE)

(73) Assignee: Braun GMBH, Kronberg (DE)

( * ) Notice: Subject to any disclaimer, the term of this patent is extended or adjusted under 35 U.S.C. 154(b) by 58 days.

(21) Appl. No.: 16/257,570

(22) Filed: Jan. 25, 2019

(65) Prior Publication Data
US 2019/0232080 A1 Aug. 1, 2019

(30) Foreign Application Priority Data

Jan. 31, 2018 (EP) .................... 18154332

(51) Int. Cl.
*A61N 5/06* (2006.01)
*A61B 18/20* (2006.01)
(Continued)

(52) U.S. Cl.
CPC .......... *A61N 5/0617* (2013.01); *A61B 18/203* (2013.01); *A61N 5/0616* (2013.01);
(Continued)

(58) Field of Classification Search
CPC ................ A61N 5/0617; A61N 5/0616; A61N 2005/0667; A61N 2005/0628;
(Continued)

(56) References Cited

U.S. PATENT DOCUMENTS 5,817,008 A * 10/1998 Rafert ................ A61B 5/14552
                                                                600/323
7,764,380 B2    7/2010 Van Hal et al.
(Continued)

FOREIGN PATENT DOCUMENTS

CN          101686819 A        3/2010
CN          108289626 A        7/2018
(Continued)

OTHER PUBLICATIONS

China First Search; China Application No. 201910094396; dated Jun. 30, 2020; National Intellectual Property Administration, PRC.
(Continued)

*Primary Examiner* — William J Levicky
*Assistant Examiner* — Alexander M Eisenberg
(74) *Attorney, Agent, or Firm* — Kevin Johnson; Stefan Schneider

(57) ABSTRACT

The present invention refers to a skin or hair treatment device for emitting intense light radiation with an integrated sensor. The device has a housing; a treatment light source, wherein the treatment light source comprises an array of a plurality of light emitting elements arranged on a substrate; a sensor system, the sensor system has at least one sensing light source for emitting sensing light and at least one light sensor for detecting the sensing light, wherein the at least one sensing light source and the at least one light sensor are directed towards a device treatment window; and a control circuit having a processor.

19 Claims, 3 Drawing Sheets

(51) Int. Cl.
*A61B 18/18* (2006.01)
*A61B 17/00* (2006.01)
*A61N 5/073* (2006.01)
*A61B 18/00* (2006.01)

(52) U.S. Cl.
CPC ............... *A61B 2017/00057* (2013.01); *A61B 2018/00476* (2013.01); *A61B 2018/00636* (2013.01); *A61B 2018/00642* (2013.01); *A61B 2018/00785* (2013.01); *A61B 2018/1807* (2013.01); *A61N 2005/0628* (2013.01); *A61N 2005/0652* (2013.01); *A61N 2005/0659* (2013.01); *A61N 2005/0667* (2013.01); *A61N 2005/073* (2013.01)

(58) Field of Classification Search
CPC ...... A61N 2005/073; A61N 2005/0652; A61N 2005/0659; A61N 2005/0632; A61N 2005/0664; A61B 2017/00057; A61B 2018/00636; A61B 2018/1807; A61B 2018/00785; A61B 18/203; A61B 2018/00642; A61B 2018/00476
USPC ............................................................ 607/88
See application file for complete search history.

(56) References Cited

U.S. PATENT DOCUMENTS

| | | | | |
|---|---|---|---|---|
| 8,749,529 B2* | 6/2014 | Powell | ................. | G06F 3/0412 345/175 |
| 8,784,407 B2 | 7/2014 | Spikker | | |
| 9,271,793 B2 | 3/2016 | Eckhouse | | |
| 9,301,588 B2 | 4/2016 | Eckhouse | | |
| 10,485,612 B2 | 11/2019 | Beerwerth et al. | | |
| 10,524,861 B2 | 1/2020 | Beerwerth | | |
| 2007/0252997 A1 | 11/2007 | Van Hal et al. | | |
| 2009/0221993 A1 | 9/2009 | Sohi | | |
| 2010/0063491 A1* | 3/2010 | Verhagen | ............... | A61B 5/417 606/9 |
| 2012/0116373 A1* | 5/2012 | Moench | ............... | A61B 18/203 606/9 |
| 2013/0120760 A1* | 5/2013 | Raguin | ............... | G06K 9/0004 356/612 |
| 2013/0265590 A1* | 10/2013 | Eisele | .................... | G01B 11/02 356/625 |
| 2016/0330390 A1* | 11/2016 | Cho | .................... | H04N 5/2252 |
| 2017/0023724 A1* | 1/2017 | Qin | ..................... | G02B 6/0051 |
| 2017/0035348 A1 | 2/2017 | Bandic et al. | | |
| 2017/0296104 A1* | 10/2017 | Ryan | ...................... | A61B 5/681 |
| 2018/0325397 A1 | 11/2018 | Presura et al. | | |
| 2019/0038913 A1 | 2/2019 | Beerwerth | | |

FOREIGN PATENT DOCUMENTS

| | | |
|---|---|---|
| EP | 2189129 B1 | 6/2013 |
| WO | 2006005443 A2 | 1/2006 |
| WO | 2013122001 A1 | 8/2013 |
| WO | 2018068550 A1 | 4/2018 |

OTHER PUBLICATIONS

European Search Report dated Jun. 11, 2018.

* cited by examiner

SKIN OR HAIR TREATMENT DEVICE AND METHOD FOR MANUFACTURING SAME

FIELD OF THE INVENTION

The present disclosure refers to a skin or hair treatment device for emitting, e.g. high intense, treatment light with an integrated sensor comprising a sensor light source (preferably a light source such as a laser diode or light emitting diode) and a light detector. Further, the present disclosure refers to a method for manufacturing such a skin or hair treatment device.

The skin or hair treatment device may be a hair management device, in particular an intense pulsed light (IPL) hair management device such as a hair removal device. By irradiating the intense light onto the skin surface and the hair, the intense light targets to the pigment melanin in the hair follicle helping to put the hair to sleep and to stop or reduce growth of the hair. The light is absorbed by the melanin and thereby converted to heat. The local heat development leads to obliteration of the root of the hair. The skin or hair treatment or hair removal device is a household appliance for a use by a private user.

BACKGROUND OF THE INVENTION

WO 2017/134553 A1 discloses such a skin or hair treatment device comprising one or more additional sensors for measuring a skin property. Further, WO 2006/005443 A2 describes a device for reducing hair growth on a subject. The device comprises a housing having an opening to allow radiation to pass there through, a treatment light source disposed within the housing, a sensor light source disposed within the housing, and an optical sensor. The said optical sensor is arranged for detecting the reflection and scattering properties of the subject at the treatment location from a reflected and scattered sensor beam emitted by the sensor light source. To this aim, the optical sensor is conductively linked to the sensor light source and the treatment light source such that the treatment light source and the sensor light source share at least a portion of an optical path disposed within the housing. The optical sensor might comprise a mechanical or optical movement sensor and a sensor for skin recognition based on optical properties of the skin (reflection and scattering).

Known skin or hair treatment devices typically have the sensor system arranged aside the treatment window, e.g. capacitive contact sensor around the window or optical skin reflection measurement beneath or aside the window with one or two measuring areas. This design has the advantage that the light source and the sensor system are not directly connected such that they do not mechanically interfere. On the other hand, this design has a drawback in that the skin color and skin contact is measured at a skin area beneath the area of treatment. This can cause under certain conditions risk of injury by the treatment light, e.g. treating a large dark spot/tattoo on the skin with risk of burns.

SUMMARY OF THE INVENTION

It is thus an object of the present invention to provide an improved skin or hair treatment device avoiding the above mentioned drawback and having a compact design. It is a further object to provide a method for manufacturing such a device.

This object is solved by a skin or hair treatment device as defined in claim 1 and a method as defined in claim 13.

A skin or hair treatment device for emitting treatment light according to the present disclosure comprises a housing, a treatment light source, e.g. an the LED module, disposed inside the housing of the treatment device for illuminating a surface, in particular a skin surface, through a device treatment window disposed outside the housing in front of the device treatment window, e.g. a protective window made of glass or plastic, wherein the treatment light source comprises an array of a plurality of light emitting elements arranged on a substrate, a sensor system disposed inside the housing of the treatment device, said sensor system comprising at least one sensing light source, e.g. one or more sensor LED's, for emitting sensing light and at least one light sensor for detecting the sensing light, wherein the at least one sensing light source and the at least one light sensor are directed towards the device treatment window, and a control circuit having a processor, the control circuit being adapted to control the treatment light source, the at least one sensing light source and the at least one light sensor. The device further comprises a circular polarizer interposed between the device treatment window and the at least one sensing light source and the at least one light sensor and a shielding interposed between the at least one sensing light source and the at least one light sensor such that sensing light is prevented from directly entering the at least one light sensor without passing the circular polarizer. The circular polarizer may be a separate part, e.g. with direct optical contact to the device treatment window, or a coating of the device treatment window itself.

The provision of the circular polarizer between the sensor module and the device window prevents direct light from the LED's entering into the e.g. photodiode of the sensor. This optical system is designed to allow only the penetration of light scattered back from the user's skin into the photodiode. E.g. in one embodiment, the light is guided by conical light guides. In another embodiment, the unwanted stray light is blocked via an opaque rim around the photodiode.

As the light source may be directly placed over the treatment area, no other optical components are involved that absorb light or redirect light away from the treatment area, leading to very low losses of light in the path between source and treatment area. Depending on the light conversion efficiency of the light source relative to other sources, like e.g. laser diodes, the low optical losses of the system lead to a higher total energy efficiency compared to the alternatives. Higher energy efficiency will lower the system costs.

DETAILED DESCRIPTION OF THE INVENTION

Figure 1:
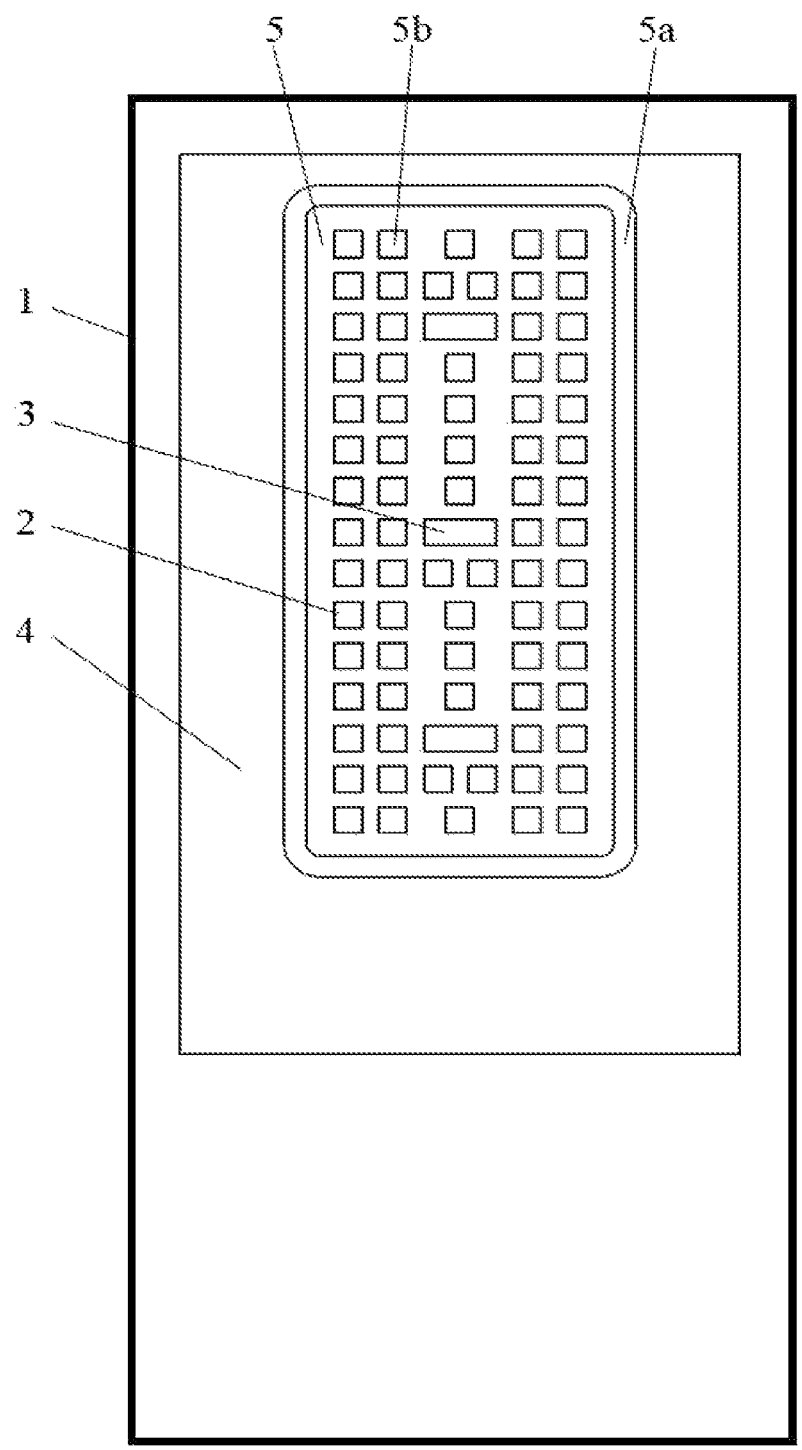
FIG. 1 schematically shows a partially opened top view a skin or hair treatment device according to a first embodiment, FIG. 2 schematically shows in a sectional view the sensor system of the device of FIG. 1, FIG. 3 schematically shows in a sectional view the sensor system of the device of FIG. 1, FIG. 4 schematically shows the treatment light source and the sensor system of a skin or hair treatment device according to a second embodiment, and FIG. 5 schematically shows a partially opened top view a skin or hair treatment device according to a third embodiment.

Before describing advantageous embodiments of the invention related to the embodiments depicted in FIGS. 1 to 5, different aspects of the invention are described more in detail. These aspects disclose further features, advantages and possibilities of use of the present invention that might be combined in any useful combination. All features described and/or shown in the drawings are subject matter of the invention, irrespective of the grouping of the features in the claims and/or their back references.

The shielding of the skin or hair treatment device may comprise a first shielding element, e.g. in the form of a rim, at least partially encasing the at least one sensing light source and/or a second shielding element, e.g. in the form of a rim, at least partially encasing the at least one light sensor. For example, the rim is made of an opaque silicone. In an embodiment of the present disclosure, a white silicone material is selected for the rim to have very low absorption for the treatment LED's and very low transmissivity for the light of the sensor LED's. The low transmissivity can be achieved via high absorption in the range of the sensor LED's or via high internal or surface light scattering.

In addition or as an alternative, the shielding may comprise at least one light focusing element, e.g. lenses, Fresnel lenses, or light guides with conical shapes. This increases the signal to noise ratio and is a measure to get a more stable and reliable measurement. The circular polarizer may in combination with the light focusing element(s) deliver a further improvement for the signal to noise ratio. The circular polarizer may be a separate part with direct optical contact to the focusing optic or a coating of the focusing optic itself.

The skin or hair treatment device may have a relatively compact design if the sensor system is arranged in the array of light emitting elements of the treatment light source interposed between and/or adjacent to the light emitting elements, i.e. the treatment LED's. In other words, an LED module intended for light based hair removal may be provided with one or more embedded sensor sub-assemblies, e.g. skin color sensors. The advantages of a light emitter array with LED's and an embedded sensor system for measuring various skin characteristics include a more uniform illumination of the treatment area, an adaptive illumination of the treatment area depending on the remission of the skin (skin color), in case of segmented LED modules, each segment can have an assigned sensor for the skin characteristic allowing the adjustment of treatment parameters for each LED segment, and an easy system integration of sensor systems for enhanced user guidance and eye safety measuring the skin characteristics directly on the spot to be treated.

The light source can be placed directly over the treatment area (behind a protective window) without additional optics (mixer, components to increase divergence, etc.) and without a diffuser. That reduces the complexity of the light delivery system of the device. It may also allow designing a smaller device as the light delivery system can be made smaller. The optical system to be included for detection purposes can be implemented with low costs.

The treatment light source may comprise a carrier having a plurality of apertures for receiving light emitting elements and an outer wall at least partially surrounding the array of light emitting elements. According to an embodiment of the disclosure, the carrier comprises the shielding. For example, the outer wall of the carrier is in sealing abutment with the device treatment window. Further, the transparent cover sheet (plastic or glass) with circular polarizing capabilities may be in close contact with the opaque aperture to prevent any direct light channel between the LED's and the photo detector.

The light emitting elements, the at least one sensing light source and/or the at least one light sensor may be embedded in transparent or translucent silicone. Preferably, the thickness of the assembly (base plate is the general base plate of the complete module) is very low. The whole assembly may have a similar height as the silicone filling between and above the LED-chips.

The treatment light source and/or the sensor may be as described in WO 2017/134553 A1 and/or in WO 2006/005443 A2. For example, the at least one sensing light source comprises a red LED and IR LED.

The control circuit with the processor may be adapted to control the sensing light source by switching off and on a sensing light, and/or to control the treatment light source by full intensity control of the high intense treatment light, and/or to control the light sensor by collecting data from the light sensor and evaluating the data.

A method for manufacturing a skin or hair treatment device, in particular the skin or hair treatment device as defined above, comprises the steps of placing light emitting elements, e.g. an array of a plurality of light emitting elements, on a substrate, placing at least one sensing light source on the substrate, placing at least one light sensor on the substrate, providing a shielding interposed between the at least one sensing light source and the at least one light sensor, providing a circular polarizer covering at least the at least one sensing light source and the at least one light sensor, providing a control circuit having a processor, the control circuit being adapted to control the treatment light source, the at least one sensing light source and the at least one light sensor, and providing a housing having a device treatment window covering at least the array of a plurality of light emitting elements, the at least one sensing light source and the at least one light sensor. The method may further comprise the step of embedding the light emitting elements, the at least one sensing light source and/or the at least one light sensor in transparent silicone such that the circular polarizer is not covered by the transparent silicone. Still further, the method may comprise the step of providing a carrier having a plurality of apertures for receiving light emitting elements and an outer wall at least partially surrounding the array of light emitting elements, such that the outer wall of the carrier is in sealing abutment with the device treatment window.

Figure 2:
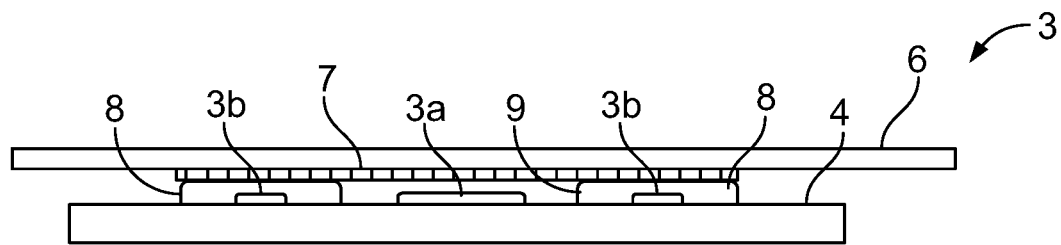
Figure 3:
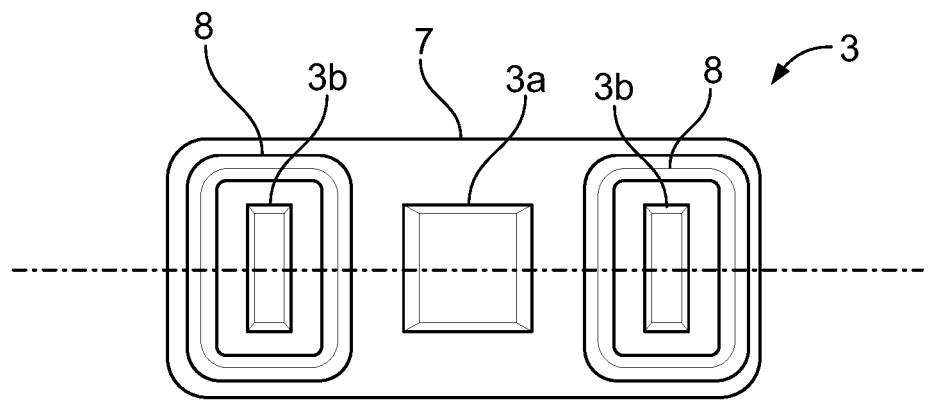

Turning now to the first embodiment depicted in FIGS. 1 to 3, a skin or hair treatment device for emitting intense light radiation comprises a housing 1 forming an outer shell for internal component parts. The housing 1 may serve as in the handle of the device.

In FIG. 1 the housing 1 is shown partially cut open such that the treatment light source 2 and a sensor system 3 are visible together with a printed circuit board 4 which forms a substrate on which the treatment light source 2 and the sensor system 3 are arranged. The printed circuit board 4 may further comprise a control circuit having a processor.

FIG. 1 further shows a carrier 5 made of an opaque material, for example white silicone. The carrier 5 comprises an outer wall 5a having a rectangular form in the depicted embodiment. The outer wall 5a forms of the outer boundaries of the treatment light source 2. The carrier 5 further comprises a portion which is arranged substantially parallel to the substrate 4 and which comprises a plurality of apertures 5b each of which is designed for receiving a light emitting element 2a, e.g. an LED. The embodiment depicted in FIG. 1 has a treatment light source 2 comprising an array of a plurality of light emitting elements 2a arranged within the rectangular boundaries defined by the outer wall 5a.

The housing 1 comprises an aperture corresponding to the outer wall 5a of the carrier 5. In other words, the printed circuit board 4 is covered by the housing 1. A device treatment window 6 is provided in the housing 1 covering the aperture. The device treatment window 6 may be in sealing contact with the outer wall 5a of the carrier, thereby defining a sealed space for the treatment light source 2 and the sensor system 3.

In the embodiment depicted in FIG. 1, the sensor system 3 comprises a total of three sensor subassemblies. The sensor subassemblies are depicted in FIGS. 2 and 3 in more detail. Each sensor subassembly comprises two sensing light sources 3b for emitting sensing light and one light sensor 3a for detecting the sensing light. The sensing light sources 3b may be LEDs, for example a red LED and an infrared (IR) LED. Other embodiments of the sensor subassembly may comprise only one sensing light source 3b or more sensing light sources 3b. The light sensor 3a comprises a photo detector, for example a photo diode or a phototransistor. Each of the sensor subassemblies is provided within the array of light emitting elements 2a of the treatment light source 2, i.e. interposed between and adjacent to the light emitting elements 2a.

The sensor subassemblies are further covered by a circular polarizer 7 which is arranged on or near the device treatment window 6. The circular polarizer 7 is adapted and arranged such that light reflected by the device treatment window 6 is blocked, whereas light scattered by a user's skin passes through the circular polarizer 7. The circular polarizer 7 may be a transparent cover sheet, e.g. plastic or glass, with circular polarizing capabilities. As an alternative to a separate circular polarizer 7, the circular polarizer 7 may be an integral part of the device treatment window 6, wherein the area with the circular polarizing capabilities of the device treatment window 6 covers at least the sensor subassemblies.

In the embodiment depicted in FIGS. 2 and 3, each of the sensing light sources 3b are surrounded by a shielding rim 8 made from an opaque material, for example silicone. The shielding rim 8 may form a reflective enclosure for each sensing light source 3b preventing a direct sensing light transmission from the sensing light source 3b to the light sensor 3a. For this purpose the shielding rim 8 is in close contact with the circular polarizer 7 to prevent any direct light channel between the LED's and the photo detector. As an alternative or in addition to the shielding rim 8 enclosing the sensing light sources 3b, a shielding rim 8 may be provided enclosing the light sensor 3a.

Taking into account that the treatment light source 2 is typically not activated simultaneously with the sensor system 3, it is not required to shield the with respect to the treatment light source 2. Thus, the photo diode of the light sensor 3a is not necessarily decoupled from the treatment LEDs 2a, but may also be surrounded by the silicon rim as the sensor LEDs 3b. The advantage of having the photodiode not decoupled from the treatment LEDs 2a is the option to use the photo diode 3a within the same setup also as a monitor diode to control the light emission of the treatment LEDs 2a.

The sensor LEDs 3b may be surrounded by a white, non-absorbing silicon shielding rim 8 made of the same material as the carrier 5 around the treatment LED area. The shielding rim 8 around the sensor LEDs 3b has the function to prevent light from directly entering the photodiode without being scattered by the user's skin. The white silicone material is selected to have very low absorption for the treatment LEDs 2a and very low transmissivity for the light of the sensor LEDs 3b. The low transmissivity can be achieved via high absorption in the range of the sensor LEDs 3b or via high internal or surface light scattering.

The space between the circular polarizer 7 and the substrate 4 and the light sensor 3a, respectively may be filled by a transparent silicone layer 9, thereby embedding the light sensor 3a and the shielding rim 8. The transparent silicone may further embed and/or cover the treatment LEDs 2a. However, the circular polarizer 7 is not covered or embedded by the transparent silicone layer 9 at the side facing towards the device treatment window 6.

Figure 4:
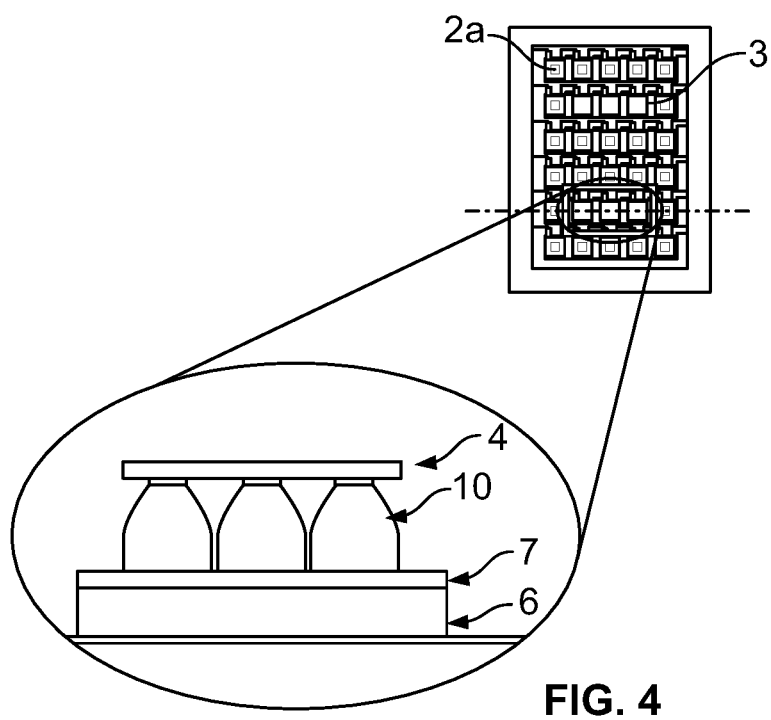

A second embodiment of the present disclosure is depicted in FIG. 4. The array of light emitting elements 2a arranged on the substrate 4 of the treatment light source 2 has slightly different dimensions compared with the first embodiment and only two sensor subassemblies of the sensor system 3 are provided within the array of treatment LEDs 2a, i.e. within the boundaries defined by the outer wall 5a of the carrier 5. As shown in the enlarged portion of FIG. 4 which is a partial sectional view along the dashed line in the main portion of FIG. 4, the sensor subassembly again comprises two sensing light sources 3b and one light sensor 3a. However, instead of the shielding rim 8 surrounding the sensing light sources 3b, shielding light focusing elements 10 are provided interposed between the sensing light sources 3b and the circular polarizer 7. The circular polarizer 7 may be a separate part with direct optical contact to the focusing optic or a coating of the focusing optic itself.

In the depicted embodiment the light focusing elements 10 are light guide cones designed to prevent direct light from the LEDs 3b entering into the photodiode 3a. An additional light guide cone may be provided interposed between the light sensor 3a and the circular polarizer 7. Additional shielding rims 8 may be provided surrounding the sensing light sources 3b and/or the light sensor or 3a.

The optical system interposed between the LED module and the device treatment window 6 is used to prevent direct light from the LEDs entering into the photodiode. The optical system is designed to allow only the penetration of light scattered back from the user's skin into the photodiode. In combination with the light focusing elements 10, the circular polarizer 7 further improves the signal to noise ratio.

Figure 5:
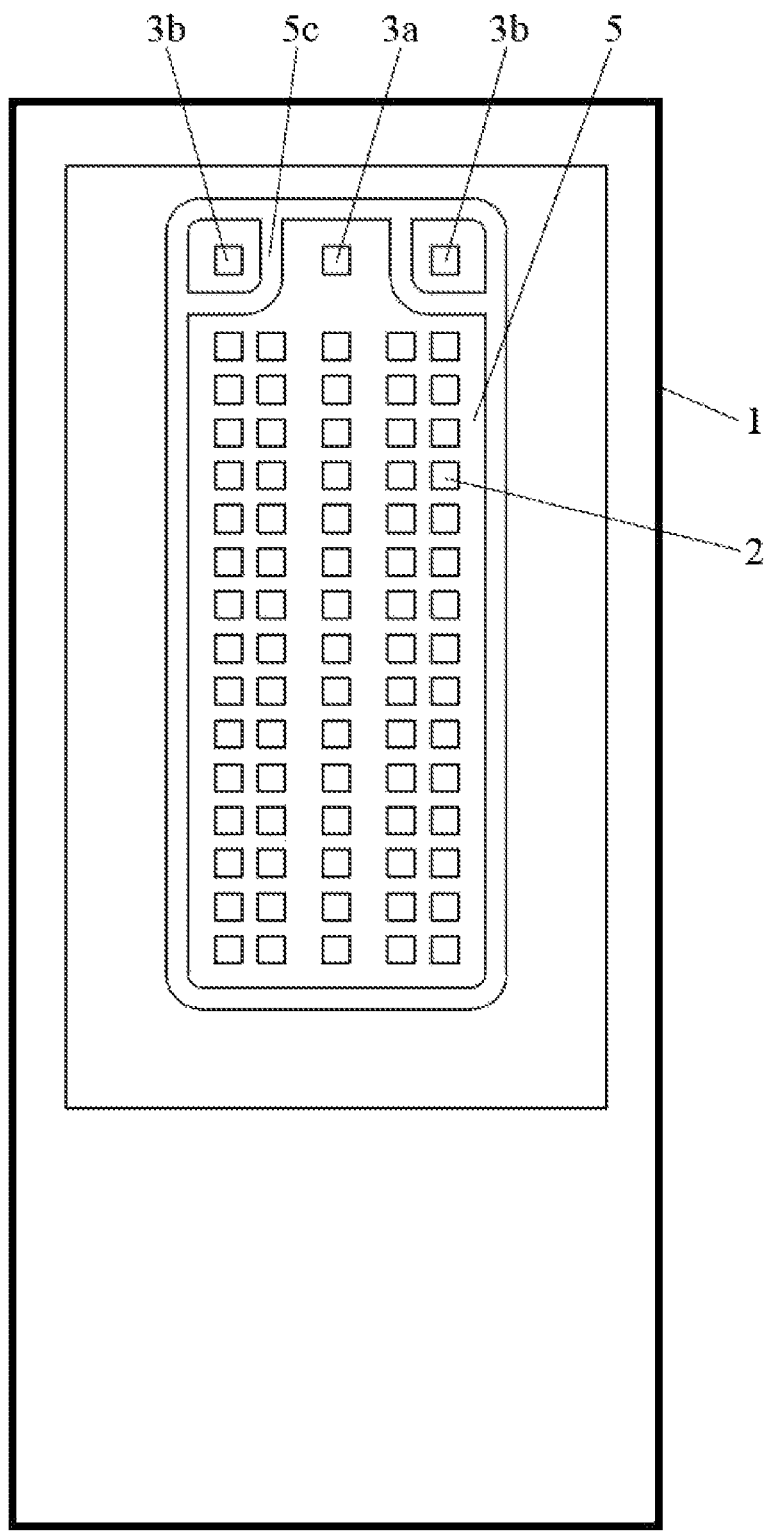

A third embodiment of the present disclosure is depicted in FIG. 5. While the size of the array of light emitting elements 2a arranged on the substrate 4 of the treatment light source 2 is about the same as in the first embodiment, the number of sensor subassemblies is only one in the third embodiment. Further, instead of being placed in the middle of the array of the light emitting elements 2a as in the first embodiment, the sensor subassembly of the third embodiment is placed in the upper corner of the array as seen in FIG. 5.

Instead of providing a separate shielding rim 8 as in the first embodiment, the Sensor LEDs 3b are surrounded be a white, non-absorbing silicon shielding rim 5c made of the same material as the carrier 5 around the treatment LED area. Omitting the separate shielding rims 8 may facilitate mounting of the skin or hair treatment device. As can be seen in FIG. 5, the photo diode of the light sensor 3a is not shielded from the treatment LEDs 2a, thus permitting use of the photo diode 3a within the same setup also as a monitor diode to control the light emission of the treatment LEDs 2a.

As can be taken from a comparison of all three embodiments, the present disclosure comprises a light delivery system for a light-based beauty device for skin treatment with a fully embedded skin color measurement system. The light delivery system may be based on semiconductor light sources, e.g. VCSEL (Vertical-Cavity Surface-Emitting Laser), VECSEL (Vertical External Cavity Surface-Emitting Laser), LED, or OLED (Organic light emitting diode) array.

The light delivery system according to the present disclosure has the advantage that the array size may be close to or about the same size of the treatment area, so that the light source can be directly placed close to the treatment area without the need for additional beam shaping optical elements. Further, the emitters may be mounted on one plain thermally highly conductive surface, e.g. a heat spreader. The heat spreader may be thermally connected to a heat sink. However, the provision of a heat spreader is optional and the light source may be mounted directly onto a heat sink. The light module, preferably an LED-module with chip on board LED-chips, has one or more embedded sensor systems to measure the light remission of the area the light source is directed to, i.e. a user's skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCE NUMERALS 1 housing
2 treatment light source
2a light emitting element (LED)
3 sensor system
3a light sensor
3b sensing light source (LED)
4 substrate (printed circuit board)
5 carrier
5a outer wall
5b aperture
5c shielding rim
6 device treatment window
7 circular polarizer
8 shielding element/rim
9 transparent silicone
10 light focusing element (light guide cone)

What is claimed is:

1. A skin or hair treatment device for emitting light radiation with an integrated sensor comprising:
   a housing;
   a device treatment window provided in the housing;
   a treatment light source disposed inside the housing of the treatment device for illuminating through the device treatment window with a surface disposed outside the housing in front of the device treatment window, wherein the treatment light source comprises a plurality of light emitting elements arranged on a substrate;
   a sensor system disposed inside the housing of the treatment device, said sensor system comprising at least one sensing light source for emitting sensing light and at least one light sensor for detecting the sensing light reflected from said surface, wherein the at least one sensing light source and the at least one light sensor are oriented towards the device treatment window; and
   a control circuit, the control circuit being adapted to control the treatment light source, the at least one sensing light source and the at least one light sensor;
   wherein the sensor system further comprises:
   a circular polarizer interposed between the device treatment window and the at least one sensing light source and the at least one light sensor; and
   a shielding interposed between the at least one sensing light source and the at least one light sensor and in contact with the circular polarizer such that sensing light is prevented from directly impinging on the at least one light sensor without passing the circular polarizer.

2. The skin or hair treatment device according to claim 1, wherein the shielding comprises a first shielding element comprising a reflective shielding element, at least partially encasing the at least one sensing light source.

3. The skin or hair treatment device according to claim 2, wherein the shielding comprises a second shielding element at least partially encasing the at least one light sensor.

4. The skin or hair treatment device according to claim 3, wherein the first shielding element or the second shielding element is made of an opaque silicone.

5. The skin or hair treatment device according to claim 1, wherein the shielding comprises at least one light focusing element.

6. The skin or hair treatment device according to claim 1, wherein the sensor system is arranged in an array of the light emitting elements of the treatment light source interposed between or adjacent to the light emitting elements.

7. The skin or hair treatment device according to claim 1, wherein the treatment light source comprises a carrier having a plurality of apertures for receiving light emitting elements and an outer wall at least partially surrounding an array of the plurality of light emitting elements.

8. The skin or hair treatment device according to claim 7, wherein the carrier comprises the shielding.

9. The skin or hair treatment device according to claim 7, wherein the outer wall of the carrier is in sealing abutment with the device treatment window.

10. The skin or hair treatment device according to claim 1, wherein the light emitting elements, the at least one sensing light source or the at least one light sensor are embedded in transparent silicone.

11. The skin or hair treatment device according to claim 1, wherein the at least one sensing light source comprises at least one red LED or at least one IR LED.

12. The skin or hair treatment device according to claim 1, wherein the control circuit, adapted to control the sensing light source, is adapted to control switching off and on the at least one sensing light source, wherein the control circuit, adapted to control the treatment light source, is adapted to control intensity of the treatment light, and wherein the control circuit, adapted to control the light sensor, is adapted to collect data from the light sensor and evaluate the data.

13. The skin or hair treatment device according to claim 1, wherein the circular polarizer is arranged on the device treatment window.

14. The skin or hair treatment device according to claim 1, wherein the circular polarizer is an integral part of the device treatment window.

15. A method for manufacturing a skin or hair treatment device, comprising the steps of:
- placing an array of a plurality of light emitting elements on a substrate;
- placing at least one sensing light source on the substrate;
- placing at least one light sensor on the substrate;
- providing a shielding interposed between the at least one sensing light source the at least one light sensor;
- providing a circular polarizer covering at least the at least one sensing light source and the at least one light sensor, wherein the shielding is in contact with the circular polarizer;
- providing a control circuit, the control circuit being adapted to control the treatment light source, the at least one sensing light source and the at least one light sensor;
- providing a housing having a device treatment window covering at least the array of the plurality of light emitting elements, the at least one sensing light source and the at least one light sensor.

16. The method according to claim 15, further comprising embedding the light emitting elements, the at least one sensing light source or the at least one light sensor in transparent silicone such that the circular polarizer is not covered by the transparent silicone on the side of the device treatment window.

17. The method according to claim 15, further comprising providing a carrier having a plurality of apertures for receiving light emitting elements and an outer wall at least partially surrounding the array of light emitting elements, such that the outer wall of the carrier is in sealing abutment with the device treatment window.

18. The method of claim 15, wherein the circular polarizer is arranged on the device treatment window.

19. The method of claim 15, wherein the circular polarizer is an integral part of the device treatment window.

* * * * *